(12) United States Patent
Chopra et al.

(10) Patent No.: US 7,924,412 B2
(45) Date of Patent: Apr. 12, 2011

(54) APPARATUS AND METHOD FOR CHARACTERIZING ELECTROPHORETIC DISPLAY MEDIUMS

(75) Inventors: Naveen Chopra, Oakville (CA); Man-Chung Tam, Mississauga (CA); Gaetano J. Lavigne, Oakville (CA); Peter M. Kazmaier, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 1290 days.

(21) Appl. No.: 11/461,188

(22) Filed: Jul. 31, 2006

(65) Prior Publication Data

US 2008/0024426 A1    Jan. 31, 2008

(51) Int. Cl.
  *G01N 21/00* (2006.01)
(52) U.S. Cl. .......................................... 356/72
(58) Field of Classification Search ............... 356/71–72; 345/107
  See application file for complete search history.

(56) References Cited

U.S. PATENT DOCUMENTS

| | | |
|---|---|---|
| 3,668,106 A | 6/1972 | Ota |
| 4,126,854 A | 11/1978 | Sheridon |
| 4,272,596 A | 6/1981 | Harbour et al. |
| 5,717,514 A | 2/1998 | Sheridon |
| 6,017,584 A | 1/2000 | Albert et al. |
| 6,113,810 A | 9/2000 | Hou et al. |
| 6,525,866 B1 | 2/2003 | Lin et al. |
| 6,531,997 B1 * | 3/2003 | Gates et al. .................. 345/107 |
| 6,577,433 B1 | 6/2003 | Lin et al. |
| 6,980,352 B1 | 12/2005 | Tam |
| 2003/0132925 A1 | 7/2003 | Lin et al. |
| 2006/0215253 A1 * | 9/2006 | Kanbe .......................... 359/296 |
| 2007/0047003 A1 * | 3/2007 | Suwabe et al. ............... 358/296 |
| 2007/0103428 A1 * | 5/2007 | Kazmaier et al. ............ 345/107 |

OTHER PUBLICATIONS

U.S. Appl. No. 11/169,924, filed Jun. 30, 2005 in the name of Ping Liu et al.
U.S. Appl. No. 11/419,436, filed May 19, 2006 in the name of Naveen Chopra et al.
U.S. Appl. No. 11/419,472, filed May 19, 2006 in the name of Man-Chung Tam et al.
U.S. Appl. No. 11/461,310, filed Jul. 31, 2006 in the name of Man-Chung Tam.

* cited by examiner

*Primary Examiner* — Tarifur Chowdhury
*Assistant Examiner* — Abdullahi Nur
(74) *Attorney, Agent, or Firm* — Oliff & Berridge, PLC (57) ABSTRACT

A method and an apparatus for measuring reflectivity, charge and/or particle mobility of electrophoretic display mediums and particles are described. The apparatus for evaluating characteristics of an electrophoretic display medium, comprising a cell for containing the electrophoretic display medium, located between conductive substrates, a voltage application unit associated with the cell, an electrometer to measure transient current, and a densitometer to measure reflectance.

9 Claims, 7 Drawing Sheets

APPARATUS AND METHOD FOR CHARACTERIZING ELECTROPHORETIC DISPLAY MEDIUMS

BACKGROUND

Described herein is an apparatus for and a method of measuring the operational effectiveness of an electrophoretic ink display device, and a method of making display devices using such method. More particularly, described is an apparatus for and a method of measuring the charges of the particles of an electrophoretic display medium of an electrophoretic display device to determine if the device is able to properly display images, and to optimize performance parameters for preparation of additional similar display devices.

An advantage associated with the apparatus and methods described herein is that a given electrophoretic ink and/or display device can be readily evaluated for effectiveness in displaying images, thereby improving quality control in the manufacture of display devices. Using the evaluation method herein, additional display devices having a same high quality display can be replicated.

Electrophoretic displays are known in the art. Known electrophoretic display devices include a device in which charged pigment particles are dispersed along with conductive additives such as charge control agents in a clear or colored insulating liquid of matching specific gravity, the dispersion being encapsulated and the encapsulated spheres being contained between two parallel conducting electrode panels. Such a display is available from E-Ink. Examples of charge control agents used have included bis-(2-ethyl hexyl)sodium sulfosuccinate and basic barium petronate (BBP). Dissociation of the charge control agent into positive and negative ionic species in the dielectric fluid results in preferential surface absorption of ions of one polarity by the particles. The particles therefore become charged. The resulting dispersion contains a complex mixture of particles including charged particles, excess free ions and counter-ions. Due to the presence of excess free ions, such electrophoretic display inks are characterized by high electrical conductivity. Conductivity has been shown to increase with concentration of the added charge control agent, and is typically 100-1000 times higher compared to the dielectric fluid. High conductivity of the ink results in increased power consumption and slower switching speed of the display.

Another known type of electrophoretic display device is comprised of charged pigment particles in a sealed (air-filled) device. Such a display is available from Fuji Xerox.

In addition, U.S. patent applications Ser. Nos. 11/419,472 and 11/419,436, each incorporated herein by reference in its entirety, describe a novel electrophoretic display device comprised of a multiplicity of individual reservoirs containing a display fluid between conductive substrates, at least one of which is transparent, wherein the display fluid comprises pigment particles in a liquid medium and wherein the display fluid has an electrical conductivity of about $10^{-11}$ to about $10^{-15}$ S/m. The display medium is desirably substantially free of charge control additives and ionic species. A significant difference between the inks for these display devices and conventional electrophoretic inks that include conductive additives is the low electrical conductivity of the novel inks due to the omission of charge directors and charge control agents from the fluid medium.

U.S. Pat. No. 4,272,596, incorporated herein by reference in its entirety, illustrates an electrophoretic display structure. The electrophoretic display device comprises a white marking material such as titanium dioxide suspended in a colloidal dispersion containing black colorant such as colloidal size iron oxide particles known as ferrofluids. Image formation is achieved electrophoretically by selective application of an electric field across the imaging suspension. In particular, a pair of electrodes associated so as to form a cavity therebetween, which cavity is filled with the aforementioned suspension medium. A source of electrical potential is coupled to the electrodes and when an electric field is applied, the marking particles form an image as they follow the field.

U.S. Pat. No. 6,113,810, incorporated herein by reference in its entirety, describes a dielectric dispersion for use in an electrophoretic display that includes a dielectric fluid, a first plurality of particles of a first color having a surface charge of a selected polarity dispersed within the dielectric fluid and a second plurality of particles of a second color having a surface charge of opposite polarity to that of the first plurality and a steric repulsion thereto preventing coagulation of the first and second plurality of particles. Each set of particles is formed with unique secondary and functional monomers. Corresponding charge control agents are added to the dispersion to establish opposite polarities on the respective particles.

U.S. Pat. No. 6,017,584, incorporated herein by reference in its entirety, discloses electrophoretic displays and materials useful in fabricating such displays. In particular, encapsulated displays are disclosed in which particles encapsulated therein are dispersed within a suspending, or electrophoretic, fluid. This fluid may be a mixture of two or more fluids or may be a single fluid. The displays may further comprise particles dispersed in a suspending fluid, wherein the particles contain a liquid. In either case, the suspending fluid may have a density or refractive index substantially matched to that of the particles dispersed therein. Application of electric fields to the electrophoretic displays affects an optical property of the display.

U.S. Pat. No. 6,577,433, incorporated herein by reference in its entirety, discloses an electrophoretic display liquid composition for use in an electrophoretic display device that has a multiplicity of individual reservoirs, each containing the display liquid of two sets of particles dispersed in a transparent liquid system as well as at least one charge director dissolved or dispersed in the liquid system, or physically embedded on the surface of the particles or chemically bonded on the surface of the surface of the particles, the two sets of particles exhibiting different, contrasting color and different charging properties from each other. The charge director(s) may include a metal salicylate compound. The particles may be modified with charge controlling agents, and may also include a set of magnetic particles. The transparent liquid system may include two immiscible liquids having different densities with the sets of particles having densities in between the densities of the two immiscible liquids such that the particles rest at an interface between the two immiscible liquids.

U.S. Pat. No. 6,525,866, incorporated herein by reference in its entirety, discloses an electrophoretic display liquid composition for use in an electrophoretic display device that has a multiplicity of individual reservoirs, each containing the display liquid of at least two sets of particles dispersed in a transparent liquid system, the at least two sets of particles exhibiting different, contrasting color and different charging properties from each other, and at least one of the sets of particles containing flow aid particles as additives upon an external surface of the particles. Preferred flow aid additives include silica and titania particles.

Electrophoretic display is thus based on the migration of charged particles under the influence of an electric field.

Characterization methods for traditional electrophoretic inks include: Q/M (commonly used in liquid toner technology), optical density measurements, and mobility measurements. Due to the complex nature of the composition of conventional electrophoretic inks containing conductive additives, the actual charged species can consist of partially adsorbed charge additives, charge control agents, excess free ions and counter-ions, along with the particles. Thus, for any system that relies on conductive additives for particle charging, there is no technique for measuring the charge on the particles alone. Moreover, no such technique is known for any other type of electrophoretic display. This makes it difficult (1) to optimize the particle making process parameters and produce toners with reproducible performance characteristics, and (2) to develop materials packages with optimal performance.

What is desired is an apparatus for and a method of measuring the parameters of an electrophoretic ink representative of operational characteristics of the ink in a display device, and/or for measuring operational effectiveness of an electrophoretic ink display, in order to confirm that the display is capable of adequately and properly displaying images, and a method of making display devices having high quality display capabilities.

SUMMARY

Described herein is a method and an apparatus for measuring reflectivity, charge and/or particle mobility of electrophoretic display inks and particles. The method and apparatus provide a useful characterization tool for monitoring the conductivity of the insulating fluid for any given electrophoretic ink system.

In embodiments, described is an apparatus for evaluating characteristics of an electrophoretic display medium, comprising a cell for containing the electrophoretic display medium, located between conductive substrates, a voltage application unit associated with the cell, an electrometer to measure transient current, and a densitometer to measure reflectance.

In further embodiments, described is a method of determining characteristics of an electrophoretic display medium, comprising arranging the electrophoretic display medium in a cell located between conductive substrates, applying a rectangular or triangular waveform switching voltage to the electrophoretic display medium in the cell, and measuring at least reflectance of the electrophoretic display medium and transient current of the electrophoretic display medium.

In further embodiments, described is a method of making electrophoretic display devices, comprising preparing a first electrophoretic display medium comprising at least one set of colored particles dispersed in a dielectric liquid substantially free of charge control additives, arranging the electrophoretic display medium in a cell located between conductive substrates, applying a rectangular or triangular waveform switching voltage to the electrophoretic display medium in the cell, measuring at least reflectance of the electrophoretic display, medium and transient current of the electrophoretic display medium, and preparing additional electrophoretic display medium to have substantially the same reflectance and transient current.

EMBODIMENTS

As the display devices that may be evaluated and prepared by the methods described herein, any suitable display device may be used. Two typical display device designs are illustrated in FIGS. 1 and 2.

Figure 1:
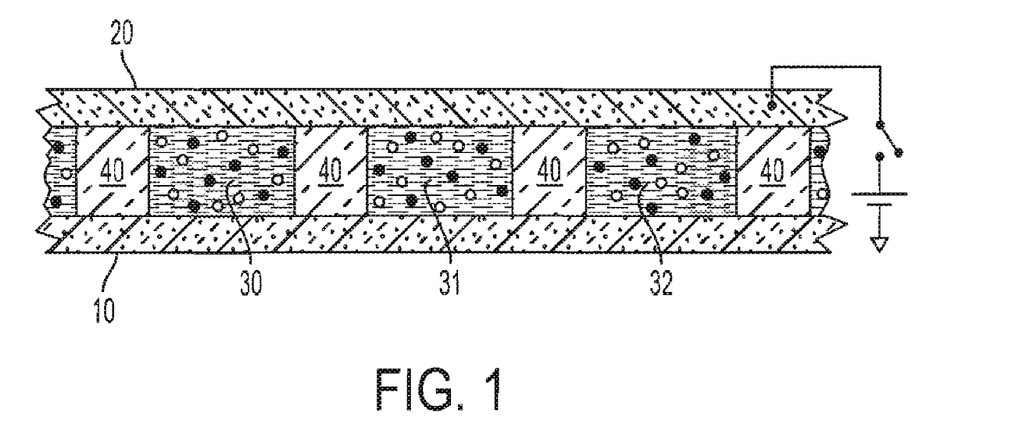
FIGS. 1 and 2 illustrate embodiments of example electrophoretic display devices.
Figure 2:
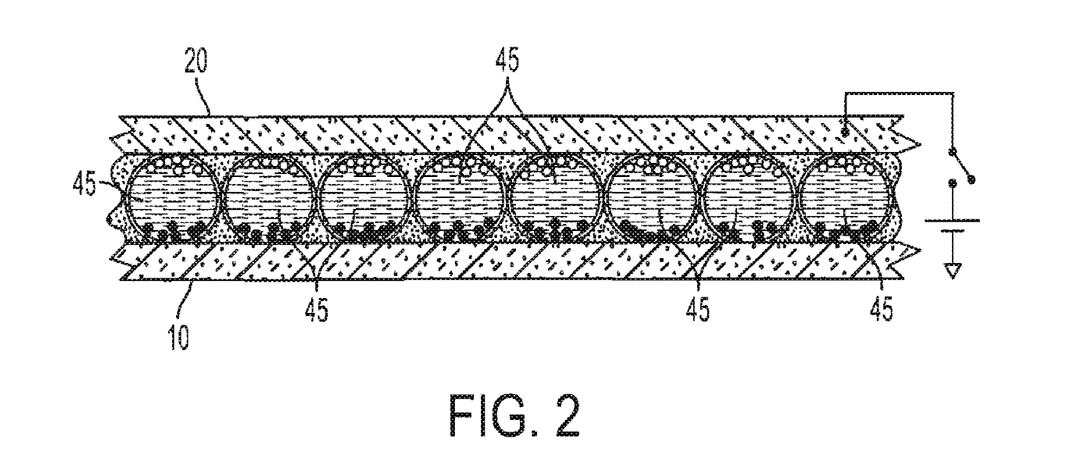

FIG. 1 illustrates an embodiment of an electrophoretic display device comprising two conductive substrates 10 and 20 disposed oppositely of each other, with an electrophoretic or display layer 40 therebetween. The display layer may have a thickness of from, for example, about 5 to about 1,000 μm, such as from about 10 to about 500 μm or from about 20 to about 350 μm.

Layer 40 may be comprised of a layer that includes spacers therein, which spacers define a multiplicity of individual reservoirs (30, 31 and 32) that each contain the display medium comprised of fluid and colored particles. A multiplicity refers to, for example, from about 2 to about 100,000,000, or potentially more, such as from about 100 to about 50,000,000 or from about 1,000 to about 1,000,000. Thus, for example, if each of the multiplicity of reservoirs is about 100 microns across, a square of 1,000×1,000 reservoirs (or about a 4 inch×4 inch display) would have about 1,000,000 total reservoirs. In this regard, each reservoir may be considered to correspond to a pixel of the device. Reservoir refers to, for example, any unit containing, or capable of containing, display medium therein, and includes, for example, units separated by a spacer device, pockets, cavities or bubbles finned in a single sheet or between two sheets, capsules or microcapsules is a sheet or layer, and the like.

In the FIG. 1 embodiment, the particles are shown to include a set of black particles and a set of white particles. However, the particles may be comprised of one set of colored particles or multiple differently colored particle sets, for example from 1 to about 10 particles sets, such as from 1 to about 6 particle sets or from about 2 to about 4 particle sets.

As the conductive substrates of the electrophoretic display device, any suitable materials may be used without limitation, for example including materials presently known and used or that may be used in the future in the art. At least one of the conductive substrates, in particular at least the top conductive substrate through which the images formed by the device may be viewed, should be transparent in order to enable such viewing. Both substrates may be transparent, if desired. The bottom or back substrate need not be transparent, and may instead be, for example, a light reflecting or light absorbing material. As suitable materials that may be used, mention may be made of conductive polymer films, for example polymer films coated with a transparent conductive material such as indium tin oxide (ITO), such as polyethylene terephthalate (PET) films, for example MYLAR (Du Pont), polyethylene napthalate (PEN) films, polyethersulfone (PES) films and the like, conductive glass films, such as ITO coated glass, and conductive thin metals. For transparency, ITO coated polymer films and glass are suitable. The substrates may either be flexible or rigid.

The substrates that sandwich the spacer layer therebetween may have a length and width corresponding to the overall length and width of the electrophoretic display device. The substrates thus may be continuous, unitary films that are not present as just separated pieces over just individual reservoirs of the display device, although a plurality of segregated substrates may also be used. The substrates may be made to be as thin as possible while still maintaining appropriate conductive properties and structural integrity. For example, the substrates may have a height, or thickness, of from about 10 microns to about 500 microns, such as from about 10 to about 250 microns or from about 20 to about 100 microns.

Between the conductive substrates are contained a multiplicity of individual reservoirs (30, 31, 32), each filled with a display medium described more fully below. Each of the individual reservoirs defines one container and/or cell of the electrophoretic display device.

In embodiments, spacers 40 as shown in FIG. 1 may be used to keep the individual reservoirs separate from one another. Any suitable spacer design may be used. For example, the spacer may be of the type described in U.S. Patent Publication No. 2003-0132925 A1, incorporated herein by reference in its entirety, or of any of the types described in U.S. application Ser. No. 11/419,436, incorporated herein by reference in its entirety. The width and/or diameter of the individual reservoirs may be from, for example, about 5 microns to about 400 microns, such as from about 5 to about 200 microns or from about 5 to about 50 microns.

The display medium to be used within the reservoirs contains particles of a size smaller than the reservoir width/in order to function.

Where the spacer layer is comprised of a multiplicity of individual reservoirs, a solid portion of the spacer separating the multiplicity of reservoirs, that is, the spacing or partition between individual reservoirs of the spacer layer, are desirably as thin as possible. Preferred spacing/partition thicknesses are on the order of, for example, about 10 microns to about 100 microns, such as from about 10 microns to about 75 microns or from about 15 to about 50 microns.

The display device may have any suitable overall length and width as desired. The electrophoretic display device may also be made to have any desired height, although a total height of from about 30 to about 1,000 microns, such as from about 30 to about 400 microns or from about 50 to about 300 microns, may be used in terms of size and ease of use of the device.

In forming the electrophoretic display device, the reservoirs, for example pockets, of the spacer layer may be filled with the display medium and the spacer layer located over a first, or bottom, conductive substrate. The filling of the reservoirs and location of the spacer over the substrate may be done ill any suitable order. In embodiments, the spacer layer may be physically attached to the first conductive substrate or intermediate films, which may be done by any suitable method. Adhesive may be used for convenience, although other attachment methods such as sputtering deposition of the conductive film may also be used. Once the reservoirs are filled with display medium and the spacer is located over the first conductive substrate, the second, or top, conductive substrate, is located over the spacer layer. In non-pocket reservoirs and/or in displays not including any intermediate layers, this may act to seal the reservoirs. The first and second substrates may also be located in association with the spacer layer in reverse order, if desired, and may also be associated with the spacer layer at the same time, for example where the spacer layer comprises a sheet of individually enclosed pockets filled with display medium. Again, the locating of the second conductive substrate in association with the spacer layer may be done by attachment, if desired, by any suitable means, including gluing with an adhesive. Additional intermediate layers may be included between the spacer layer and conductive substrates as desired, and thus the location and/or attachment as described above need not be a direct attachment or association of the spacer to the conductive substrates.

Another embodiment of a suitable electrophoretic display device is illustrated in FIG. 2. In FIG. 2, the electrophoretic display device again comprises conductive substrates 10 and 20 disposed oppositely of each other. However, in this embodiment, the layer between the substrates is comprised of a multiplicity of microcapsules 45 that have electrophoretic display medium encapsulated therein. The microcapsules may be held in a suitable matrix material. A similar electrophoretic display device utilizing microcapsules is described in U.S. Pat. No. 6,017,584, incorporated herein by reference in its entirety. The microcapsules may be made to have a size (diameter) of from, for example, about 5 microns to about 1,000 microns, such as from about 5 to about 200 microns or from about 5 to about 50 microns.

In this embodiment, the microcapsules may be prepared and filled with the display medium, and then the microcapsules are fixed or glued onto one or both of the conductive substrates, or onto intermediate layers between the microcapsules and the substrates, or onto other layers of microcapsules in the device if multiple layers are used. Desirably, the microcapsules form a monolayer (a layer having a thickness substantially corresponding to the average diameter of the microcapsules of that layer) in the display layer of the display device. However, multiple layers, for example 2 to about 10 or 2 to about 4, may also be used. In the layer(s), the microcapsules may be arranged in abutting, side-by-side relationship.

For making the microcapsules, any suitable method of encapsulation may be used. Suitable methods and materials are described in U.S. application Ser. No. 11/419,436, incorporated herein by reference in its entirety.

Additional electrophoretic display device designs may also be evaluated by the method and apparatus herein even though not specifically shown. For example, a design in which the display device is comprised of at least one layer, for example one to ten layers such as one to four layers or one to two layers, and specifically one layer, of a binder, for example a transparent binder, containing therein multiple individual cavities or pockets that contain the display medium. Such a display device is shown and described with respect to FIGS. 14 and 15 in U.S. application Ser. No. 11/419,436, incorporated herein by reference.

As the display medium to be used and evaluated, any display medium known in the art may be used. The medium may comprise one or more liquids or fluids, for example insulating fluids, or it may comprise air or one or more inert gases. The set(s) of colored particles are dispersed within the liquid or air medium.

In embodiments, the medium is comprised of a fluid. The fluid may be either clear/transparent, or it may exhibit a visible color, for example a different, contrasting color from the color(s) exhibited by the sets of particles dispersed therein. A colored fluid is typically used in a display employing a single set of colored particles, for example white particles, with the color of the fluid being a contrasting color other than white. If colored, the fluid may be colored by any suitable means in the art, including through the inclusion of suitable dispersible colorants such as dyes and/or dispersible pigments therein.

In embodiments, the fluid of the display medium and the set(s) of particles therein may have densities that are substantially matched, for example wherein the densities of these materials are within about 10% of each other, or more specifically within 5% of each other or within 2% of each other. In other embodiments, the fluid may comprise two immiscible fluids having different densities such that the first immiscible fluid having a density less than that of the second immiscible fluid rests on top of the second immiscible fluid, and each of the sets of particles has a density in between the densities of the two immiscible fluids such that the particles rest at an interface between the two immiscible fluids.

The fluid may comprise from about 10% to about 95% by weight of the display medium, for example from about 30% to about 90% or from about 40% to about 80% by weight of the display medium.

The choice of fluid may be based on concerns of chemical inertness, density matching to the particles to be suspended therein and/or chemical compatibility with the particles. In embodiments, the suspending fluid may have a low dielectric constant, for example, about 4 or less, such as about 0.5 to about 2. The viscosity of the fluid may be relatively low at the temperatures of operation in order to permit the particles to move therein, for example under the influence of an electrical field. In embodiments, the fluid may have a kinematic viscosity in the range of about 0.25 centistokes to about 10 centistokes, for example from about 0.5 centistokes to about 5 centistokes or from about 1 centistoke to about 2 centistokes, at about room temperature (about 23° C. to about 27° C.). The fluid may be dielectric and substantially free of ions. The fluid also may have minimum solvent action on the colored particles therein, and a specific gravity substantially equal to the colored particles, for example within about 10% of each other. Additionally, the fluid may be chosen to be a poor solvent for some polymers, which is advantageous for use in the fabrication of particles because it increases the range of polymeric materials useful in fabricating particles.

The fluid may include therein a thermally reversible gelling agent having a melting point temperature of at least about 35° C., for example as described in co-pending application Ser. No. 11/169,924, incorporated herein by reference in its entirety.

Organic solvents such as halogenated organic solvents, saturated linear or branched hydrocarbons, silicone oils, and low molecular weight halogen-containing polymers are a few suitable types of fluids that may be used. Organic solvents may include, for example, epoxides such as, for example, decane epoxide and dodecane epoxide, vinyl ethers such as, for example, cyclohexyl vinyl ether, and aromatic hydrocarbons such as, for example, toluene and naphthalene. Halogenated organic solvents may include, for example, tetrafluorodibromoethylene, tetrachloroethylene, trifluorochloroethylene, 1,2,4-trichlorobenzene, carbon tetrachloride, mixtures thereof and the like. These materials may have high densities. Hydrocarbons may include, for example, decane, dodecane, tetradecane, xylene, toluene, hexane, cyclohexane, benzene, the aliphatic hydrocarbons in the ISOPAR™ (Exxon), NORPAR™ (a series of normal paraffinic liquids from Exxon), SHELL-SOL™ (Shell), and SOLTROL™ (Shell) series, naphtha, and other petroleum solvents. These materials may have low densities. Examples of silicone oils include octamethyl cyclosiloxane and higher molecular weight cyclic siloxanes, poly(methyl phenyl siloxane), hexamethlyldisiloxane and polydimethylsiloxane. These materials may have low densities. Low molecular weight halogen-containing polymers may include, for example, poly(chlorotrifluoroethylene) polymer or KRYTOX™ polymers (Dupont).

Typically, hydrocarbon fluids such as ISOPAR M are used for electrophoretic ink applications due to their low cost, good dielectric strength, low volatility, and nonreactivity. In embodiments, the fluid may be a nonswelling fluid such as a silicone fluid. A commercially available silicone fluid includes DOW 200, a polydimethylsiloxane polymer available from Dow Corning. Other examples of suitable silicone fluids include polydimethylsiloxane fluids available from Gelest Corporation such as trimethylsiloxy terminated fluids DMS-T00, DMS-T01, DMS-T01.5, DMS-T02, DMS-T03, DMS-T05, DMS-T07, DMS-T11; cyclomethicones such as SIO6700.0, SID2650.0, SID4625.0 (also known as D4, D5, and D6 fluids, respectively); phenylmethylsiloxanes such as PMM-0011, PDM-7040; fluorosilicones such as SIB1816.0; polydiethylsiloxanes such as DES-T03, DES-T11; branched and low viscosity phenyltris(trimethylsiloxy)silane fluids such as SIP6827.0, phenethyltris(trimethylsiloxy)silane fluids such as SIP6722.8, and the like.

In embodiments, the fluid is substantially free of charge control additives and other ionic species that may affect the charging behavior of the display medium and/or the particles dispersed therein. However, in other embodiments, the fluid may contain additives such as surface modifiers to modify the surface energy or charge of the particles, such as charge control agents, dispersants, and/or surfactants.

In embodiments, the display medium includes at least one set of particles exhibiting substantially the same color. The display medium may be comprised of one set of colored particles, including at least two, such as from two to ten or from two to four, sets of differently colored particles dispersed in the fluid. Color refers to, for example, the overall absorption characteristic within the range of wavelengths of the electromagnetic spectrum. Substantially the same color herein refers to, for example, particles exhibiting substantially the same hue and contrast (darkness/lightness) as other particles in the set. Colored particles of different sets of particles in the display medium exhibit a color, that is, an absorption characteristic, different from each other. For example, if a first set of particles exhibits a yellow color, then a second differently colored set of particles will exhibit a different shade (hue and/or contrast) of yellow or a different color altogether, for example such as cyan or magenta.

A display medium may include two sets of differently colored particles, for example black particles and white particles. In embodiments, the display medium comprises at least three differently colored sets of particles. As examples, the three sets of colored particles may comprise the three subtractive primary colors yellow, cyan and magenta, or may comprise red, blue and green. An example display medium containing four sets of differently colored particles may comprise yellow, cyan, magenta and black. Additional differently colored sets of particles, for example for highlight coloring, may be included as additional sets of colored particles in any embodiment described herein.

Each set of same colored particles in the display medium may comprise from about 5% to about 50% by weight, for example from about 5% to about 40% or from about 5% to about 3% by weight, of the display medium.

In embodiments, described is a low electrical conductivity electrophoretic display medium, for example having a conductivity on the order of about $10^{-11}$ to about $10^{-15}$, such as from about $10^{-12}$ to about $10^{-14}$ S/m or from about $10^{-12}$ to about $10^{-13}$ S/m. The conductivity of the display medium is thus comparable to that of the dielectric fluid. The particles of the display medium may become charged by the application of a high electric field thereto, which may also be referred to as field-induced or in situ charging, in which particle charging is dependent on, for example, the field strength and the charging time (or number of charging cycles). Following charging, the particles may have a charge (charge to mass ratio) on the order of microcoulombs (μC) per gram (that is, on the order of $10^{-6}$ C/g), such as from about ±0.1 to about ±20 C/g, from about ±0.2 to about ±10 μC/g or from about ±0.3 to about ±5 μC/g.

The display medium, including the fluid and particle sets therein, of embodiments herein may thus be made to be substantially free of charge control additives and similar excess ionic species affecting the charging characteristics and/or conductivity of the display medium. Substantially free of ions herein refers, for example, to the display medium being free of ionic species to the extent that the aforementioned conductivity values may be achieved. As a result, the display medium herein is able to exhibit the aforementioned low conductivity properties.

In other display mediums, the particles are typically charged by adding a charge control agent, which is capable of ionic dissociation, to the fluid during preparation of the non-aqueous ink dispersion. Dissociation of the charge control agent into positive and negative ionic species in the dielectric fluid results in preferential surface absorption of ions of one polarity by the particles, and the particles therefore become charged. The resulting dispersion contains a complex mixture of particles including charged particles, excess free ions and counter-ions. Due to the presence of excess free ions, the electrophoretic ink is also characterized by high electrical conductivity, which increases with concentration of the added charge control agent and is typically 100-1000 times higher compared with the dielectric fluid.

As the particles of the display medium, any particle made by any suitable process may be used, so long as the particles are capable of exhibiting the low charge property discussed above. Thus, particles made by both physical grinding methods, in which the material of the particles is formed as a mass that is then crushed and ground to the desired average particle size, and chemical build-up methods, in which the particles are grown individually within a reaction medium to the desired average particle size, both of which types of methods are well known in the toner art, may be used. The particles may be made to have an average size of from, for example, about 5 nm to about 100 μm, such as from about 10 nm to about 50 μm or from about 0.5 μm to about 25 μm. The particles typically have a size less than the size of the reservoirs of the display device in which the display medium will be contained so that the particles are free to move within the reservoirs.

The particles may be neat pigments, dyed (laked) pigments, pigment/polymer composites, dyed or pigmented agglomerated polymer particles and the like. As the colorant of the particles, dyes, pigment, mixtures of dyes, mixtures of pigments or mixtures of dyes and pigments may be used. Particles and/or colorant of particles may also include laked, or dyed, pigments, in which a dye is precipitated on the particles or the particles are stained with a dye such as metal salts of readily soluble anionic dyes, for example dyes of azo, triphenylmethane or anthraquinone structure containing one or more sulphonic or carboxylic acid groupings precipitated by a calcium, barium or aluminum salt.

Typical manufacturing techniques for the above particles are drawn from the liquid toner and other arts and include ball milling, attrition, jet milling, and the like. A pigmented polymer particle may be made by, for example, compounding a pigment in the polymer. The composite material is then (wet or dry) ground to a desired size. It may then optionally be added to a carrier liquid and milled under high shear for several hours to a final particle size and/or size distribution.

Chemical processes that may be used in forming the particles include, for example, emulsion aggregation, dispersion polymerization, mini-or micro-emulsion, polymerization, suspension polymerization, precipitation, phase separation, solvent evaporation, in situ polymerization, or any process of microencapsulation.

Polymers that may be used for the pigmented particles include, for example, polystyrene, polyethylene, polypropylene, phenolic resins, ethylene-vinyl acetate copolymers, polyesters, polyacrylates, polymethacrylates, ethylene acrylic acid or methacrylic acid copolymers, acrylic copolymers and terpolymers and the like. Specific example include, for example, polyethylene, polypropylene, polymethylmethacrylate, polyisobutylmethacrylate, polystyrene, polybutadiene, polyisoprene, polyisobutylene, polylauryl methacrylate, polystearyl methacrylate, polyisobornyl methacrylate, poly-t-butyl methacrylate, polyethyl methacrylate, polymethyl acrylate, polyethyl acrylate, polyacrylonitrile, and copolymers of two or more of these materials.

While pigment/polymer composite particles, for example composite particles created by a physical-chemical process such as grinding/attrition of pigment/polymer or by surface treatment/grafting of stabilizing polymeric groups on the surface, may be used herein, such composite particles may have polydisperse particles that exhibit variable charging characteristics. Thus, in embodiments, the particles for the display medium are emulsion aggregation particles, for example including polyester resin based emulsion aggregation particles and styrene-acrylate or acrylate resin based emulsion aggregation particles. Such particles are chemically grown and tend to be substantially monodisperse in size and substantially spherical in shape. Another advantage to emulsion aggregation particles is that the particle surface is substantially completely passivated by the binder resin, which may eliminate the contribution of the colorant, such as pigment, to the particle charge. Desirable particles are described in detail in U.S. application Ser. No. 11/419,436, incorporated herein by reference in its entirety.

In operating the display device so as to form an image therewith, an electric field, in particular a reversible direct current or an alternating current, is applied via the electrodes in order to move desired ones of the sets of colored particles in the display medium at desired locations of the display device to be displayed so as to display a desired color surface thereof to a viewer. The individual reservoirs, or groups of individual reservoirs, for example a group of from about 1 to about 50 reservoirs or from about 1 to about 10 reservoirs, may be independently addressable, that is, a separate electric field may be applied to each individual or small group of reservoirs in order to generate an appropriate color at that individual location of the device. Appropriate larger sets or groups of different ones of the reservoirs may also be associated with a same driving electrode, if desired. Thus, in a display, each reservoir or a group of reservoirs may represent a pixel or sub-pixel of an image, and each pixel or sub-pixel may thus be separately controlled to generate a desired overall image from the device. Each pixel can be individually addressed, and a full page image can thus be generated. Control methods, including hardware/software, for controlling each reservoir and/or electrode of the display device in a manner enabling an overall image to be shown are known in the display arts, and any such control method may be applied herein. To permit individual addressability, the size of the electrodes may be the same as or smaller than the size of the individual reservoirs or a small group of reservoirs of the display device, enabling individual control of each. In this manner, the electric field applied to each can be individually controlled. Also, the size of the electrodes can be different (for example, larger than) from the size of the reservoirs, thereby enabling more than one reservoir to be controlled by a single electrode. Thus, the pattern of the electrodes does not need to line up with the pattern of individual reservoirs of the display layer. Any of the foregoing can be done by, for example, appropriate patterning of the conductive path on one or more of the conductive substrates. An example of the patterning of electrodes can be found in, for example, U.S. Pat. No. 3,668,106, incorporated herein by reference in its entirety.

In electrophoretic ink displays, during manipulation under the electrical field, particles of a same color set in the medium first move from a first side of the reservoir, for example, move off of the electrode on a first side of the reservoir, when a threshold voltage is met and surpassed for that set of colored particles. The particles move toward the opposite side of the reservoir and come to rest on this opposite side, for example on the electrode on the side of the device opposite the first side. This translation of the particles of a same color set across the reservoir causes a change in the reflectance value exhibited by the reservoir. The translational movement also induces current flow through the external circuit. The methods herein measure both current and reflectance as a function of time in characterizing the electrophoretic display inks.

In embodiments, described is an apparatus and method for determining charge and mobility of particles in an electrophoretic display medium, and for determining the performance of a display device incorporating the display medium. When a display medium is found to provide excellent display performance, the procedures for making that medium may then be replicated in order to reliably produce additional display devices having excellent performance.

Figure 3:
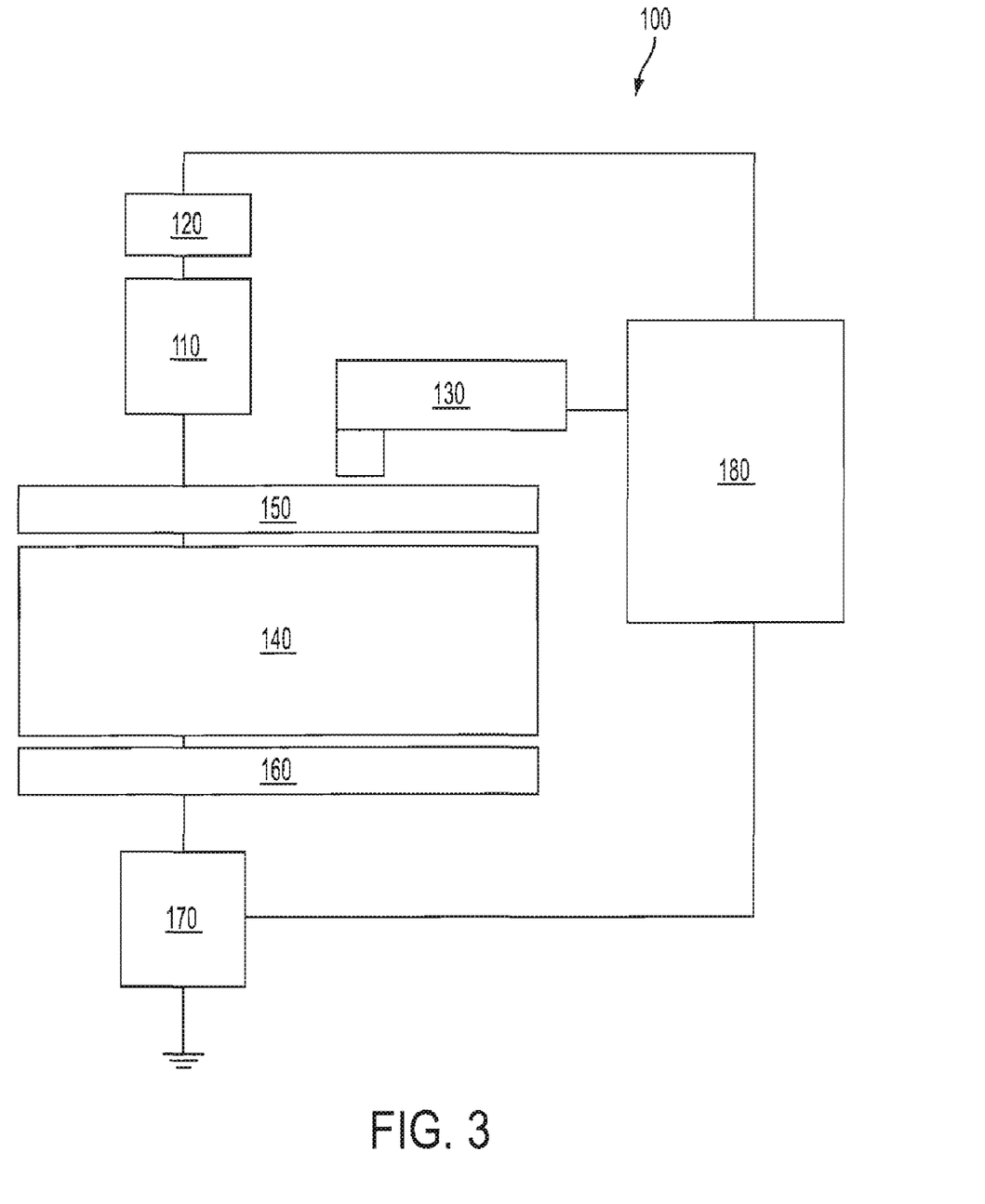
FIG. 3 illustrates a device for measuring the characteristics of an electrophoretic ink.

FIG. 3 is a schematic diagram of an apparatus that may be used in evaluating a formed display device or a cell filled with electrophoretic display medium. As shown in FIG. 3, the display device, comprised of display layer 140 sandwiched between conductive substrates 150 and 160, may be located within the apparatus 100. An appropriate electric field may be generated via control generator 120 and power supply 110. The power supply/generator may be used to apply either a square/rectangular waveform voltage or a triangular waveform voltage to the display device. The charging (current) is measured by electrometer 170, which monitors the transient current. A commercial electrometer such as a Keithley electrometer may be used. The reflection densitometer 130 measures the change in reflectance of the display as the electric field is switched back and forth by the electric field. A commercial densitometer such as a Macbeth TR927 may be used. The system may be controlled by, for example, LabVIEW interface software and a PC 180, which performs processes such as process control as well as data acquisition, analysis and plotting.

Where it is desired to evaluate a display medium prior to incorporation into a display device, a similar apparatus to that shown in FIG. 3 may be used. The device may comprise a cell arranged in a location of the device of FIG. 3 where the display layer is situated. The cell includes an inlet through which display medium may be fed or injected into the cell. The cell also desirably includes means to remove air or gas bubbles from the medium fed into the cell, for example such as a gasket sealed vacuum chamber. The cell size is desirably adjustable, that is, the cell gap between electrodes is adjustable such that the distance between electrodes in the cell can be changed, in order to accommodate various particle sizes and size distributions, and to create varying electrical fields (volts/micron) through variance of the cell gap. A fixed area electrode may also be associated with the cell, thereby permitting calculation of charge/mass (Q/M) values, as known in the art.

In the method of evaluating the display medium using the above-described apparatus, the dynamic reflectivity of the display medium is evaluated as follows. The explanation is detailed with respect to a display medium comprised of a set of black particles and a set of white particles, but may be equally carried out on any one, two, or more, colored particle set display mediums as will be understood by practitioners in the art. The black and white particles are pigment/polymer composite particles. A typical white pigment used is titanium dioxide. A typical black pigment used is carbon black or magnetite. Polymers that can be used include copolymers such as styrene-butyl acrylate and methyl-methacrylate-butyl acrylate. Surface additives may be blended with the particles, such as surface modified colloidal silica and/or titania particles. To measure dynamic reflectivity, a rectangular/square wave (hereinafter rectangular wave for convenience) or triangular wave switching voltage is applied to the display device. Current may also be measured when applying the switching voltage waveform.

Figure 4:
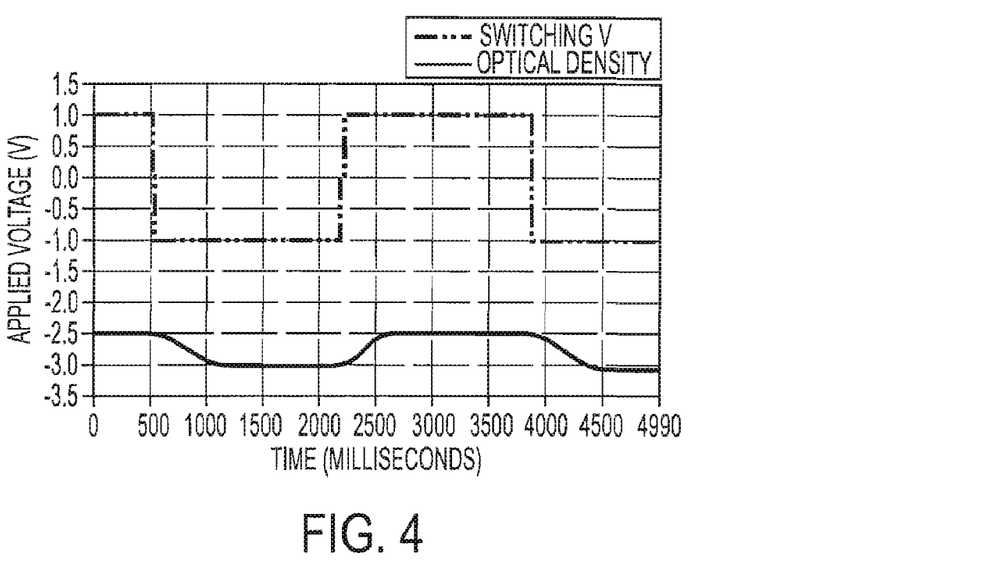
FIGS. 4 and 5 are plots associated with a determination of the dynamic reflectivity of an electrophoretic display medium comprised of particles in an insulating liquid substantially free of charge control additives.

For example, a rectangular waveform is applied to the device, or cell containing the display medium, as shown in FIG. 4. The setup involves the application of a rectangular wave voltage oscillating between a + and a − voltage. This causes all the particles in the cell to detach from the electrode by overcoming the adhesive forces and migrating towards the opposite electrode in response to the electric field. The densitometer measures the reflectance of the area as a function of time using data acquisition software. The outputs of the dynamic reflectivity square waveform method may include white reflectance, black reflectance and/or contrast ratio, switching voltage, switching time and/or switching voltage threshold, and mobility and charge of particles.

The dynamic reflectivity measurement comprises application of a rectangular waveform switching voltage. For example, as shown in FIG. 4, the voltage is switched abruptly between a positive polarity and a negative polarity. In FIG. 4, the Y-axis is referring to the applied voltage used in the test cell, and the units are in volts. So, for the upper curve, a square wave potential is being applied between +1 V and −1 V. However, the waveform is measuring the voltage signal being sent by the function generator, and this signal is passed through an amplifier, so the applied voltage is actually 100 times greater. The X-axis indicates time in milliseconds. So, for FIG. 4, the voltage scale ranges from +150 V to −350 V and the time is ranging from 0 to 4990 milliseconds, or from 0 to about 5 seconds.

Figure 5:
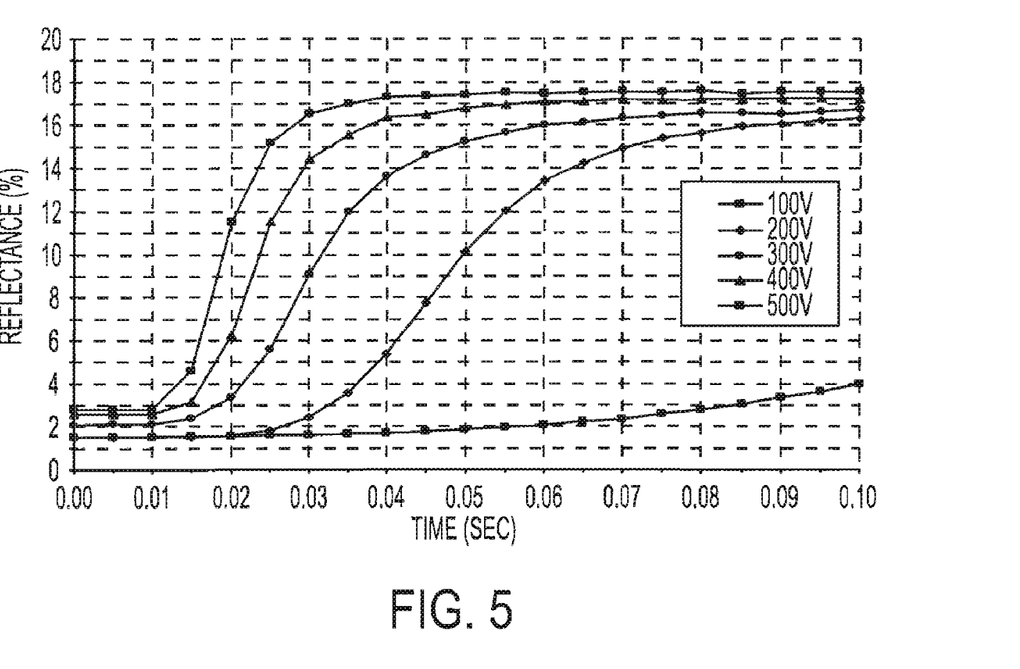

Upon application of the electric field sufficient to overcome the resting position of the particles of the display medium, the particles translate across the cell/reservoir. Thus, in switching the voltage through a display device containing black and white particles, the particles are made to display either a white color of high reflectance or a black color of low reflectance. This may be made to occur as a result of the set of black particles and the set of white particles having an opposite polarity such that switching the voltage switches the respective positions of each set of particles relative to the other set. The reflectance is monitored by the reflection densitometer, and the results are shown in FIG. 5 (FIG. 4 also including a trace of the change in optical density in the curve below the rectangular waveform to illustrate the change of reflectance with the change in voltage). The Y-axis of the lower curve in FIG. 4 shows the direct measurement of the output voltage from the densitomer, which is related to the optical density of a material being measured using an experimental calibration curve of the densitomer. From the optical density, the reflectance is then calculated as known in the art.

FIG. 5 is a plot of reflectance R, measured as a percentage of light detected upon reflection, as measured over time upon application of the rectangular waveform switching voltage in FIG. 4. Reflectance data is desirably gathered for a number of different switching voltages. As seen in FIG. 5, the reflectance changes most rapidly at the highest applied voltages.

Figure 6:
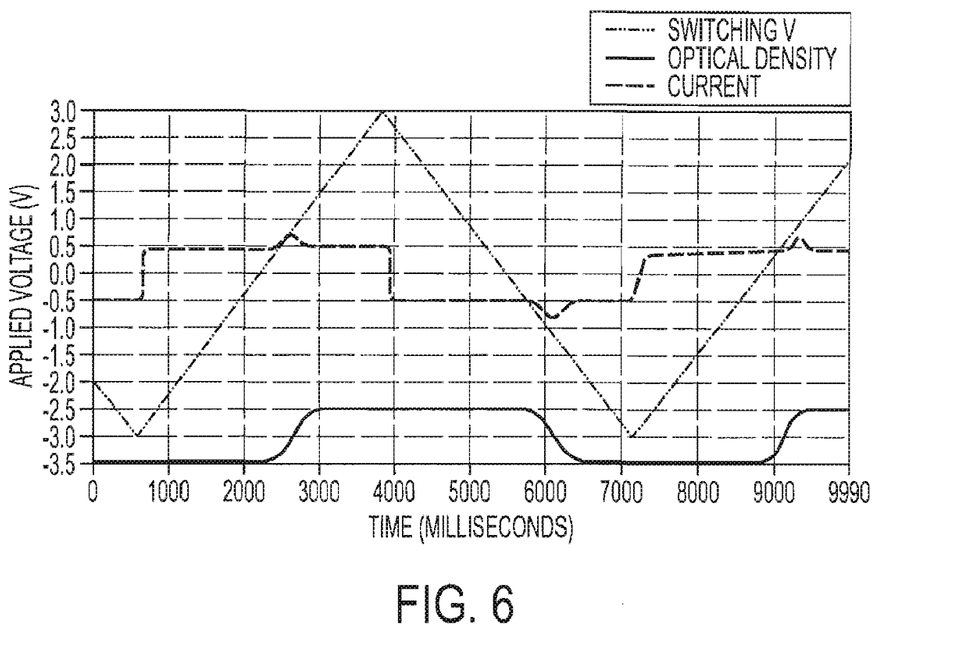
FIGS. 6 and 8 are plots associated with a determination of the dynamic current, FIG. 7 again associated with reflectance, of an electrophoretic display medium comprised of particles in an insulating liquid substantially free of charge control additives.

Measurement of dynamic current may be done through application of a triangular waveform through the display device or cell containing the display medium. For example, as shown in FIG. 6, the voltage applied is switched at a steady rate, and thus a trace of the voltage versus time curve shows a triangular (steady up and down) pattern as in FIG. 6. FIG. 6 illustrates a switching of the voltage between +3 V and −3 V (from +300 V to −300 V due to the amplifier) at a rate of about 3.3 seconds (going from − to + or + to −) over a time of from 0 to about 10 seconds (9990 milliseconds). The X-axis is again time in milliseconds. The upper curve, in the middle of the triangular waveform, in FIG. 6 illustrates the measured current. The Y-axis of this curve illustrates the direct measurement of the output voltage from the electrometer, which is proportional to the current of the sample. For example, the dynamic current is given by the reading multiplied by a scale factor of $10^{-8}$ amperes. The lower curve below the triangular waveform again represents optical density. The sweep rate of the switching voltage needs to be selected such that it is not too rapid. If too rapid, the particles will begin to move back toward the substrate from which they started before the translational jump is completed.

The setup for dynamic current measurements involves the application of a triangular wave voltage that ramps up and down between a + and a − voltage. As the voltage increases, highly charged particles detach from the electrodes and start to translate towards the opposite electrode when a threshold voltage is reached, by overcoming the adhesive force between the particles and the substrate/electrode. This is then followed by particles of lesser charge. Translational motion of the particles will induce current flow through the external circuit, which stops when all particles complete translation. Both current and reflectance may be measured as a function of time. The measured current curve exhibits characteristic peaks, which correspond to charged species translating across the cell, that cause the rise/fall in reflectance. This measurement can provide information about particle charge and charge distribution, and is very useful in characterizing the electrodynamics of the display medium particles for material development and optimization.

Figure 7:
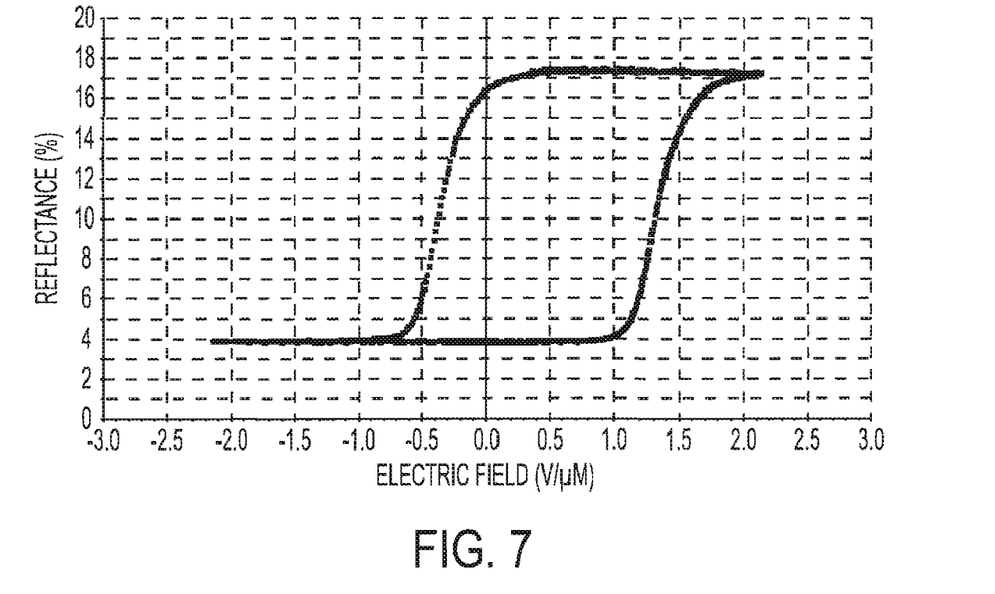
Figure 8:
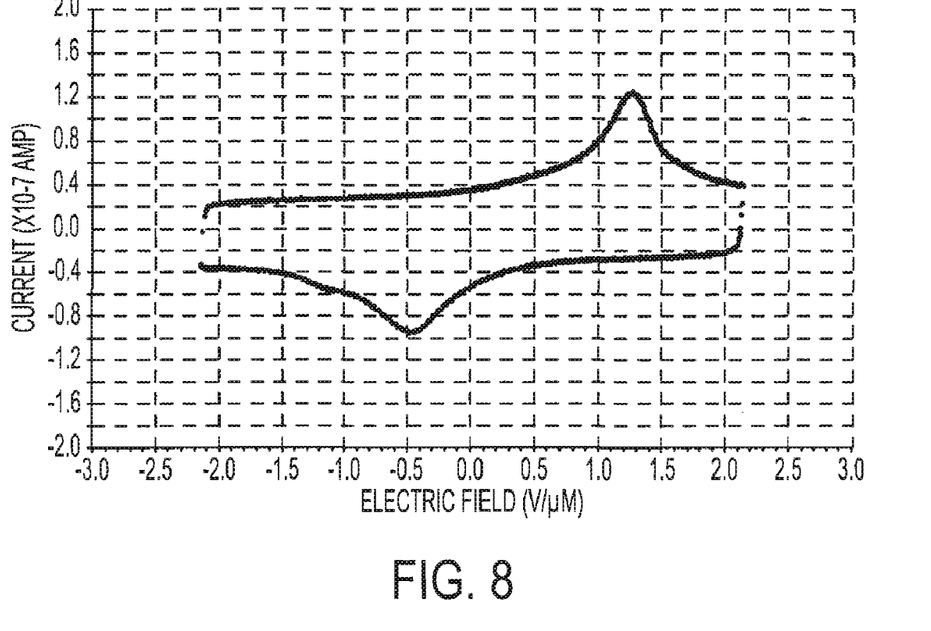

As the switching voltage is applied in the triangular waveform, the current through the device is measured via the electrometer or other suitable device. The reflectance may here again also be measured, as illustrated in FIG. 7 (reflectance vs. electric field). A plot of the current (as current vs. electric field) is shown in FIG. 8. In both cases, electric field is in units of V/μm, where μm represents the distance between electrodes in the display device or cell. The current plot of FIG. 8 shows a single current bump or spike therein. This occurs at the point where the particles are jumping across the gap from one side of the reservoir or cell to the other. The peak is rounded instead of a straight up and down spike as a result of the charge distribution among different particles not being completely uniform. The charge of the particles is reflected in the current versus electric field trace.

By reviewing the measured reflectance and current results, it can be determined if the particles of the display medium are appropriately charged and have a suitable charge distribution to permit reliable switching at the intended voltages of operation of the display device. Substantially complete reflectance changes are desired within a time of less than about 0.5 seconds, for example from about 0.01 to about 0.4, or from about 0.01 to about 0.3 seconds. Moreover, the change in reflectance is desirably accompanied by a single spike in the current versus electric field curve at the time of the change in reflectance, for example as shown in FIG. 8.

The voltage waveform, reflectance and current as a function of time may be plotted together in a single plot, if desired.

The contrast ratio may be calculated by taking the white state reflectivity divided by the dark state reflectivity, for example as plotted in the reflectance versus electric field plot of FIG. 7. The upper half of the curve represents the reflectivity in the white state, and is approximately 17%, and the lower half of the curve represents the reflectivity in the dark state and is approximately 4%. Thus, the contrast ratio for this device would be about 17/4=4.25:1.

The display device and display medium are stable if the current versus electric field plot and reflectance versus electric field plot does not change over time.

Upon determination that a given display medium provides acceptable charge and display parameters as discussed above, additional identical display mediums and display devices may be prepared with an assurance that the additional display devices would most likely also have high quality display capabilities and characteristics.

Figure 9:
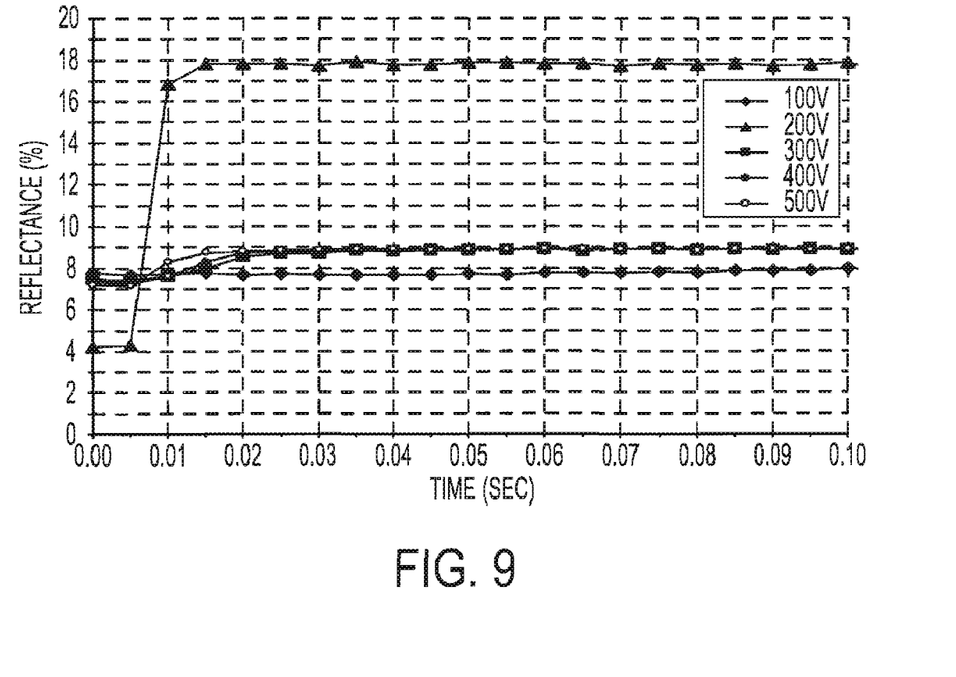
FIGS. 9 and 10 are plots of reflectance and current for an electrophoretic display comprised of particles in air.
Figure 10:
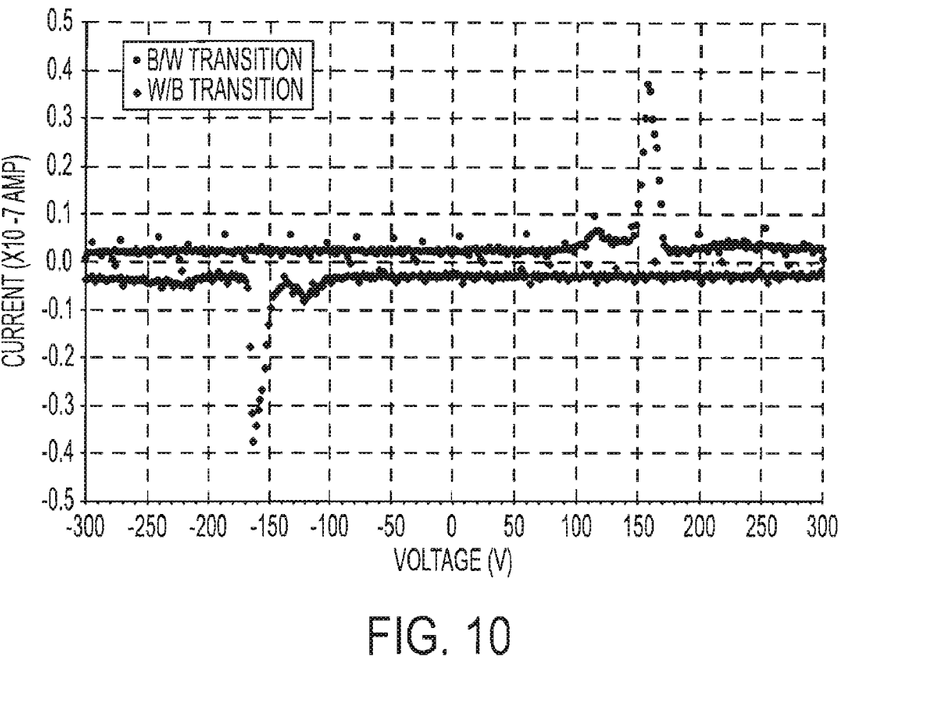
Figure 11:
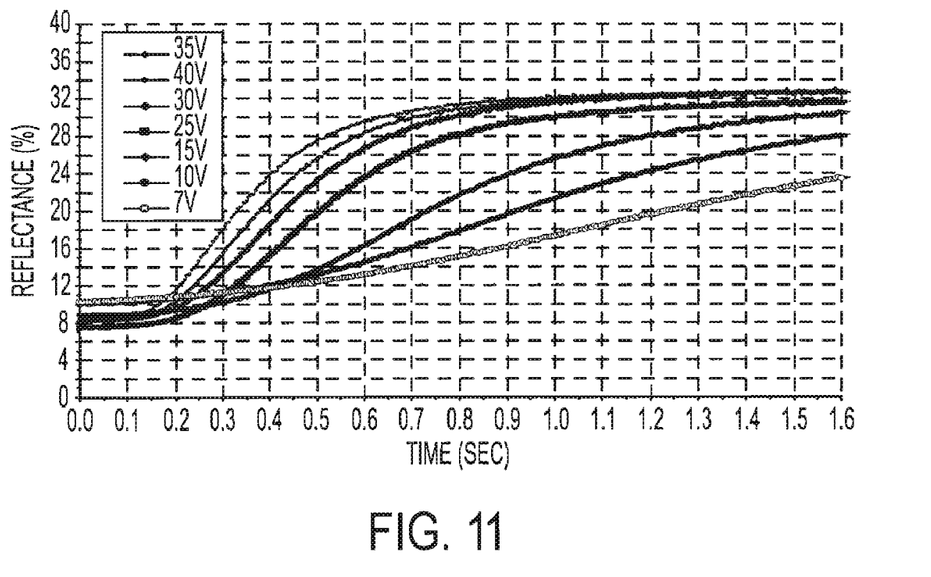
FIGS. 11 and 12 are plots of reflectance and current for an electrophoretic display comprised of particles dispersed with charge control agents in an insulating liquid.
Figure 12:
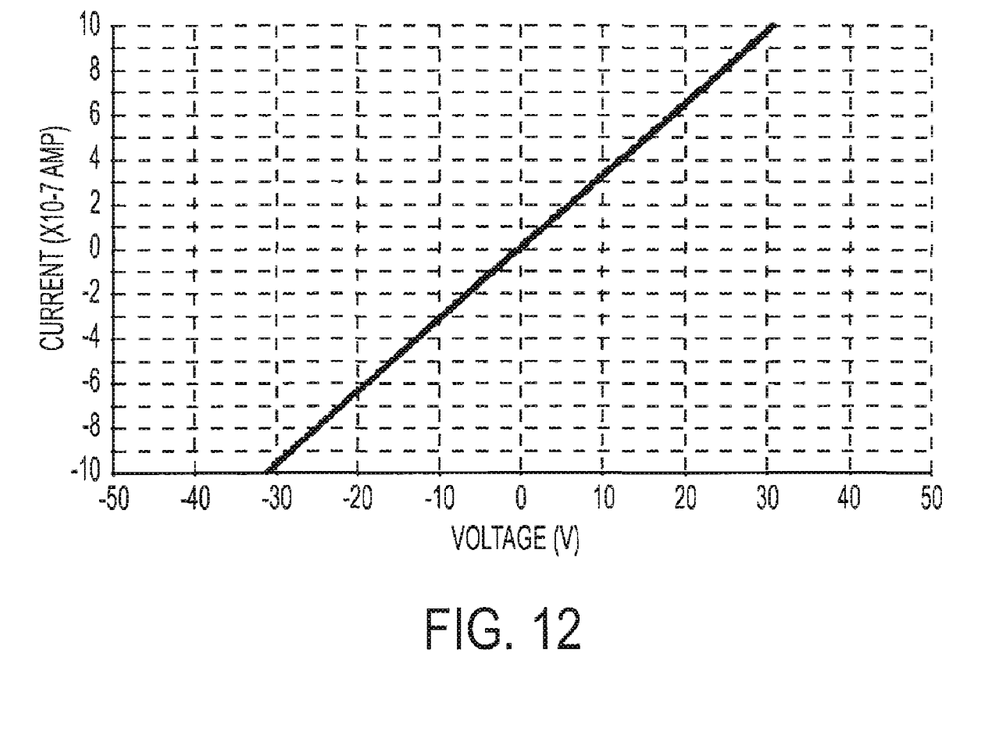

As examples of the utility of the methods and apparatus herein, dynamic reflectivity and dynamic current measurements were made on two other electrophoretic displays, (1) a toner display of particles in air (FIGS. 9 and 10) and (3) a black and white display comprised of particles dispersed with charge control agents in an insulating liquid (FIGS. 11 and 12).

For the display of particles in air, from the reflectance vs. time plot (FIG. 9), very low reflectance changes over time are seen, presumably due to particle adhesion. The current vs. electric field plot (FIG. 10) shows a flat baseline slope, indicative of very low background conductivity, $\sim 9 \times 10^{-14}$ S/m (a desirable feature that is not surprising, given that the device does not contain any fluid). Also observed in the current vs. field plot is the presence of more than one current peak, indicative of multiple species of particle types with various charge distributions in the device (not a desired feature).

For the display of particles dispersed with charge control additives in an insulating liquid, the reflectance vs. time curve (FIG. 11) shows a gradual reflectance change at very low operating voltages, but a slow response (indicated by the gradual rise trend in the curves, not a desirable feature). The current vs. field trace (FIG. 12) shows a steep slope (ohmic response), indicative of a highly conductive system (not a desirable feature). It is not possible to determine the charge of the particles in this system because the current peak is masked within this steep slope line. The high conductivity is expected based on the use of charge directors and charge control agents in the fluid medium.

The method and apparatus herein thus provide, for the first time, systematic study of electrophoretic display medium particle electro-optic and electro-dynamic behavior. The technique of dynamic current allows for the determination of the particle charge as well as the background conductivity of the insulating fluid in electrophoretic display mediums, necessary for material development and optimization. The method and apparatus provides a versatile diagnostic tool for probing the performance of all electrophoretic systems.

It should finally be noted that the apparatus as shown in FIG. 3 herein and described above may also be similarly used to evaluate display properties of characteristics of other display devices, for example gyricon display devices such as described in co-pending application Ser. No. 11/461,310, entitled "Method For Measuring Effective Operation of Gyricon Display Device," filed on even date herewith, and incorporated by reference herein in its entirety.

It will be appreciated that the various of the above-disclosed and other features and functions, or alternatives thereof, may be desirably combined into many other different systems or applications. Also, various presently unforeseen or unanticipated alternatives modifications, variations or improvements therein may be subsequently made by those skilled in the art, and are also intended to be encompassed by the following claims.

What is claimed is:

1. A method of determining characteristics of an electrophoretic display medium, comprising:
   arranging the electrophoretic display medium in a cell located between conductive substrates,
   changing between a rectangular or triangular waveform to apply switching voltage to the electrophoretic display medium in the cell, and
   measuring at least reflectance of the electrophoretic display medium and transient current of the electrophoretic display medium,
   when selecting the rectangular waveform to apply switching voltage, characteristics of the electrophoretic display medium determined consist of white reflectance, black reflectance, contrast ratio, switching voltage, switching time, switching voltage threshold, mobility of particles, and charge of particles, and
   when selecting the triangular waveform to apply switching voltage, characteristics of the electrophoretic display medium determined consist of white reflectance, black reflectance, contrast ratio, mobility of particles, charge of particles, and charge distribution.

2. The method according to claim 1, wherein the method further comprises measuring the charge of particles or the mass of particles of the electrophoretic display medium.

3. The method according to claim 1, wherein the reflectance transitions between a higher reflectance state of a first color of particles in the electrophoretic display medium and a lower reflectance state of a second color of particles in the electrophoretic display medium as the switching voltage switches between a positive polarity and a negative polarity.

4. The method according to claim 1, wherein the transient current exhibits a single spike when particles of the electrophoretic display medium translate from a first side of the cell to an opposite side of the cell under influence of the switching voltage.

5. A method of making electrophoretic display devices, comprising:
   preparing a first electrophoretic display medium comprising at least one set of colored particles dispersed in a dielectric liquid substantially free of charge control additives,
   arranging the first electrophoretic display medium in a cell located between conductive substrates,
   changing between a rectangular or triangular waveform to apply switching voltage to the first electrophoretic display medium in the cell,
   measuring at least reflectance of the first electrophoretic display medium and transient current of the first electrophoretic display medium, and
   preparing a second electrophoretic display medium to have substantially the same reflectance and transient current, wherein
   when selecting the rectangular waveform to apply switching voltage, characteristics of the electrophoretic display medium determined consist of white reflectance, black reflectance, contrast ratio, switching voltage, switching time, switching voltage threshold, mobility of particles, and charge of the particles and
   when selecting the triangular waveform to apply switching voltage, characteristics of the electrophoretic display medium determined consist of white reflectance, black reflectance, contrast ratio, mobility of particles, charge of particles, and charge distribution.

6. The method according to claim 5, wherein the transient current exhibits a single spike when particles of the electrophoretic display medium translate from a first side of the cell to an opposite side of the cell under influence of the switching voltage.

7. The method according to claim 5, wherein the reflectance changes in a time of less than about 0.10 seconds under influence of the switching voltage.

8. The method according to claim 7, wherein the transient current exhibits a single spike when the reflectance changes.

9. The method according to claim 5, wherein the reflectance changes in a time of about 0.01 to about 0.05 seconds under the influence of the switching voltage.

* * * * *